US008982351B2

(12) United States Patent
Kim et al.

(10) Patent No.: US 8,982,351 B2
(45) Date of Patent: Mar. 17, 2015

(54) APPARATUS FOR MEASURING TRANSMITTANCE OF COVER GLASS FOR PHOTOVOLTAIC CELL

(71) Applicant: Samsung Corning Precision Materials Co., Ltd., Gyeongsangbuk-do (KR)

(72) Inventors: Misun Kim, ChungCheongNam-Do (KR); Taeho Keem, ChungCheongNam-Do (KR); Hyun Woo Kim, ChungCheongNam-Do (KR); Taekmin Kwon, ChungCheongNam-Do (KR); Siho Seong, ChungCheongNam-Do (KR)

(73) Assignee: Samsung Corning Precision Materials Co., Ltd., Gumi-Si (KR)

( * ) Notice: Subject to any disclaimer, the term of this patent is extended or adjusted under 35 U.S.C. 154(b) by 96 days.

(21) Appl. No.: 13/742,734

(22) Filed: Jan. 16, 2013

(65) Prior Publication Data

US 2013/0222804 A1 Aug. 29, 2013

(30) Foreign Application Priority Data

Jan. 16, 2012 (KR) ........................ 10-2012-0004764

(51) Int. Cl.
*G01N 21/00* (2006.01)
*G01N 21/59* (2006.01)
*G01N 21/958* (2006.01)

(52) U.S. Cl.
CPC .............. *G01N 21/59* (2013.01); *G01N 21/958* (2013.01)
USPC .......................................................... 356/432

(58) Field of Classification Search
CPC ...................................................... G01N 21/59
USPC .......................................................... 356/432
See application file for complete search history.

(56) References Cited

U.S. PATENT DOCUMENTS 3,628,872 A * 12/1971 Miranda ........................ 356/432
3,632,226 A * 1/1972 Filby et al. ..................... 356/435
3,895,155 A * 7/1975 Shukuri et al. ................. 428/206
5,859,705 A * 1/1999 Benedetto et al. ............ 356/336

(Continued)

FOREIGN PATENT DOCUMENTS

JP 2012047732 A * 3/2012
KR 10-2004-0089199 A 10/2004

(Continued)

OTHER PUBLICATIONS

Gotch, Shawn Michael (Application Note: Measuring the Light Transparency of Smart Glass; ECE 480: Senior Design, Michigan State University; Nov. 19, 2010).*

*Primary Examiner* — Roy M Punnoose
(74) *Attorney, Agent, or Firm* — McDermott Will & Emery LLP

(57) ABSTRACT

An apparatus for measuring the transmittance of a piece of cover glass for a photovoltaic cell which can measure an accurate transmittance irrespective of whether or not the cover glass has a pattern and irrespective of the shape of the pattern. The apparatus includes a light source part disposed in front of the piece of cover glass. The light source part directs light into the piece of cover glass. A detector is disposed in the rear of the piece of cover glass, and detects light that has been directed into the piece of cover glass and then has passed through the piece of cover glass. The detector is disposed within a range where the intensity of the light that has passed through the piece of cover glass is uniform.

8 Claims, 4 Drawing Sheets

AIR
GLASS
SOLAR CELL

(56) References Cited

U.S. PATENT DOCUMENTS

| | | | | |
|---|---|---|---|---|
| 2011/0292373 | A1* | 12/2011 | Witting et al. | 356/51 |
| 2013/0188188 | A1* | 7/2013 | Kwon et al. | 356/432 |

FOREIGN PATENT DOCUMENTS

| | | | |
|---|---|---|---|
| KR | 10-2007-0099216 | A | 10/2007 |
| KR | 10-2009-0021977 | A | 3/2009 |

* cited by examiner

APPARATUS FOR MEASURING TRANSMITTANCE OF COVER GLASS FOR PHOTOVOLTAIC CELL

CROSS REFERENCE TO RELATED APPLICATION

The present application claims priority from Korean Patent Application Number 10-2012-0004764 filed on Jan. 16, 2012, the entire contents of which application are incorporated herein for all purposes by this reference.

BACKGROUND OF THE INVENTION

1. Field of the Invention

The present invention relates to an apparatus for measuring the transmittance of a piece of cover glass for a photovoltaic cell, and more particularly, to an apparatus for measuring the transmittance of a piece of cover glass for a photovoltaic cell which can measure an accurate transmittance irrespective of whether or not the cover glass has a pattern and irrespective of the shape of the pattern.

2. Description of Related Art

Recently, as a countermeasure to the shortage of energy resources and to environmental pollution, the development of high-efficiency photovoltaic cells is underway on a large scale. A photovoltaic cell is a key device for photovoltaic power generation that directly converts solar energy into electric energy. At present, photovoltaic cells are applied to a variety of fields, including electrical/electronic products, power supplies for houses and buildings and industrial facilities.

Here, a piece of cover glass is used in order to protect a photovoltaic cell from an external environment, such as contamination or impacts. The transmittance of the cover glass may be decisive for the entire efficiency of the photovoltaic cell. Therefore, an enormous amount of research and development is underway in order to increase the transmittance of cover glass. Here, technologies for increasing the transmittance of cover glass may be generally divided into two approaches. The first approach is to form an antireflection (AR) coating on the surface of cover glass, and the second approach is to form a pattern on the surface of cover glass, as shown in FIG. 1, which results in the light-trapping effect.

However, as shown in FIG. 2, since a piece of patterned glass which has a pattern on the surface thereof scatters light, part of the light is not detected by a detector. This makes it difficult to measure the transmittance of patterned glass.

Accordingly, the related art has a problem in that it is almost impossible to obtain an accurate transmittance measurement on patterned glass using a typical spectrometer.

The information disclosed in the Background of the Invention section is only for the enhancement of understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide an apparatus for measuring the transmittance of a piece of cover glass for a photovoltaic cell which can measure an accurate transmittance irrespective of whether or not the cover glass has a pattern and irrespective of the shape of the pattern.

In an aspect of the present invention, provided is an apparatus for measuring the transmittance of a piece of cover glass for a photovoltaic cell. The apparatus includes a light source part disposed in front of the piece of cover glass, the light source part directing light into the piece of cover glass; and a detector disposed in the rear of the piece of cover glass, the detector detecting light that has been directed into the piece of cover glass and then has passed through the piece of cover glass. The detector is disposed within a range where the intensity of the light that has passed through the piece of cover glass is uniform.

In an exemplary embodiment, the light source part may direct collimated light into the piece of cover glass.

In an exemplary embodiment, the light source part may include a light source and a lens which collimates light that has been emitted from the light source.

Here, a pin-hole may be disposed between the light source and the lens.

In addition, the light source may be implemented as a halogen lamp.

In an exemplary embodiment, the range where the intensity of the light is uniform may be such that the detector is distant from the piece of cover glass by 15 mm or less.

In an exemplary embodiment, the detector may include a photodiode and a digital multimeter connected to the photodiode.

In an exemplary embodiment, the piece of cover glass may have a pattern formed on a front surface thereof.

According to embodiments of the invention, it is possible to measure the transmittance of various types of cover glass, including a piece of cover glass that is antireflection (AR)-etched, without a loss in light irrespective of whether or not the cover glass has a pattern and irrespective of the shape of the pattern, such as a pyramidal pattern, a wave-like pattern or a mist-like pattern.

In addition, it is possible to measure the transmittance of a piece of large cover glass by point detection or scan detection. Therefore, the apparatus for measuring the transmittance of a piece of cover glass can be applied online to a process.

The methods and apparatuses of the present invention have other features and advantages which will be apparent from, or are set forth in greater detail in the accompanying drawings, which are incorporated herein, and in the following Detailed Description of the Invention, which together serve to explain certain principles of the present invention.

DETAILED DESCRIPTION OF THE INVENTION

Reference will now be made in detail to an apparatus for measuring the transmittance of a piece of cover glass for a photovoltaic cell according to the present invention, various embodiments of which are illustrated in the accompanying drawings and described below.

In the following description of the present invention, detailed descriptions of known functions and components incorporated herein will be omitted when they may make the subject matter of the present invention unclear.

Figure 1:
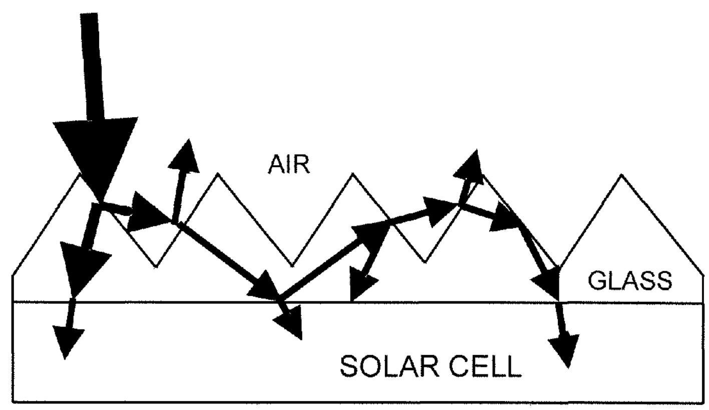
FIG. 1 is a schematic view showing the light-trapping effect of a piece of typical cover glass.
Figure 2:
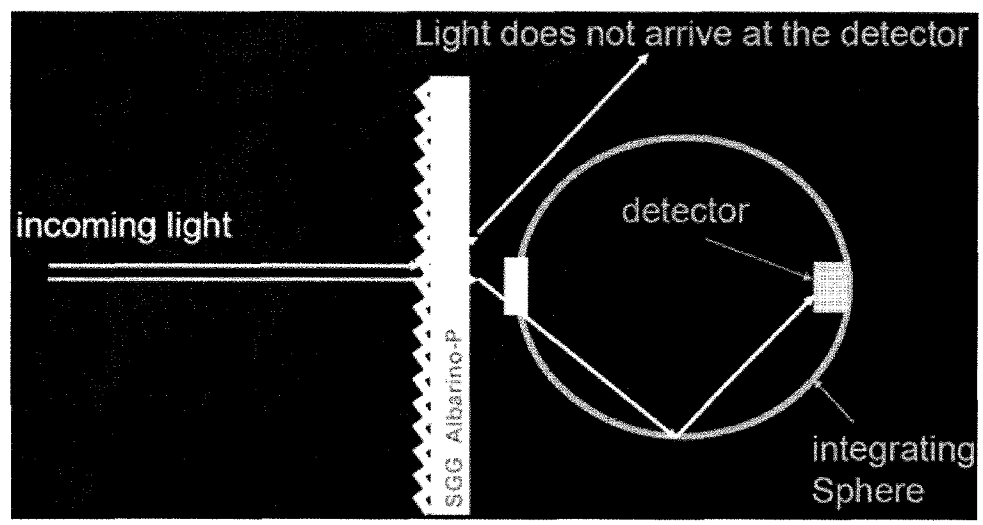
FIG. 2 is a schematic view showing a method of measuring the transmittance of a piece of cover glass of the related art.
Figure 3:
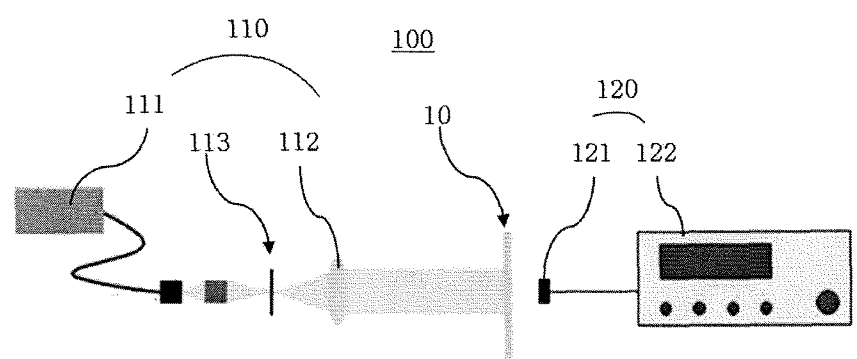
FIG. 3 is a schematic view showing the configuration of an apparatus for measuring the transmittance of a piece of cover glass for a photovoltaic cell according to an embodiment of the invention.

As shown in FIG. 3, an apparatus 100 for measuring the transmittance of a piece of cover glass for a photovoltaic cell is an apparatus which measures the transmittance of various types of cover glass 10 including a piece of cover glass 10 that is antireflection (AR)-etched. The apparatus 100 for measuring the transmittance measures the transmittance of the cover glass 10 irrespective of whether or not the cover glass 10 has a pattern 10*a* and irrespective of the shape of the pattern 10*a*, such as a pyramidal pattern, a wave-like pattern or a mist-like pattern. The apparatus 100 for measuring the transmittance includes a light source part 110 and a detector 120.

The light source part 110 is a device which generates light that is used in measuring the transmittance of the cover glass 10, and is disposed in front of the cover glass 10. In this state, the light source part 110 directs light into the cover glass 10 through the front surface of the cover glass 10.

Here, the cover glass 10 is mounted on one surface of a photovoltaic cell, for example, a solar cell, and serves to protect the photovoltaic cell from the external environment, such as moisture, dust or damage. The cover glass 10 can be made of tempered glass, for example, soda-lime glass ($SiO_2$—CaO—$Na_2O$) or borosilicate glass ($SiO_2$—$B_2O_3$—$Na_2O$), of which the contents of Na and Fe can be lowered depending on applications. In order to increase the transmittance of the cover glass 10, a porous layer or the pattern 10*a*, such as a pyramidal pattern, a wave-like pattern or a mist-like pattern, may be formed on the surface of the cover glass 10. Here, when the transmittance of the cover glass 10 the surface of which is etched or has the pattern 10*a* is measured after it is manufactured, incoming light is scattered by the porous layer or the pattern 10*a*. Therefore, it is impossible to obtain accurate transmittance measurements using a spectrometer of the related art. In contrast, the apparatus 100 for measuring the transmittance according to an embodiment of the invention can obtain accurate measurements on various types of cover glass 10 irrespective of whether or not the pattern 10*a* is present and irrespective of the shape of the pattern 10*a* using the light source part 110 and the detector 120.

The light source part 110 which directs light into the cover glass 10 is intended to introduce collimated light into the cover glass 10 in order to obtain accurate transmittance measurements. For this, the light source part 110 may include a light source 111 and a lens 112. Here, the light source 111 is a device which emits white light, and can be implemented as a halogen lamp. The lens 112 serves to collimate the light that has been emitted from the light source 111. In addition, a pin-hole 113 may be disposed between the light source 111 and the lens 112. The pin-hole 113 converges the light that has been emitted from the light source 111 to the lens 112 while increasing the intensity of the light.

The detector 120 is a device which detects the light that has passed through the cover glass 10 after the light has been emitted from the light source 111, has passed through the lens 112, and then has been incident into the cover glass 10. Here, the light that is directed into the cover glass 10 from the lens 112 is collimated light, whereas the light that has passed through the cover glass 10 becomes scattered light when the cover glass 10 is etched or has the pattern 10*a* thereon.

Figure 4:
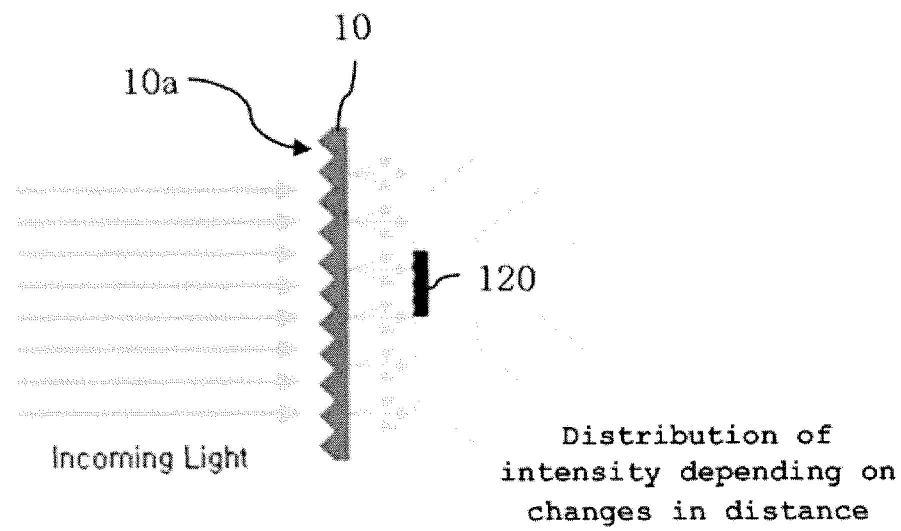
FIG. 4 is a schematic view showing a transmittance measuring process of an apparatus for measuring the transmittance of a piece of cover glass for a photovoltaic cell according to an embodiment of the invention.
Figure 5:
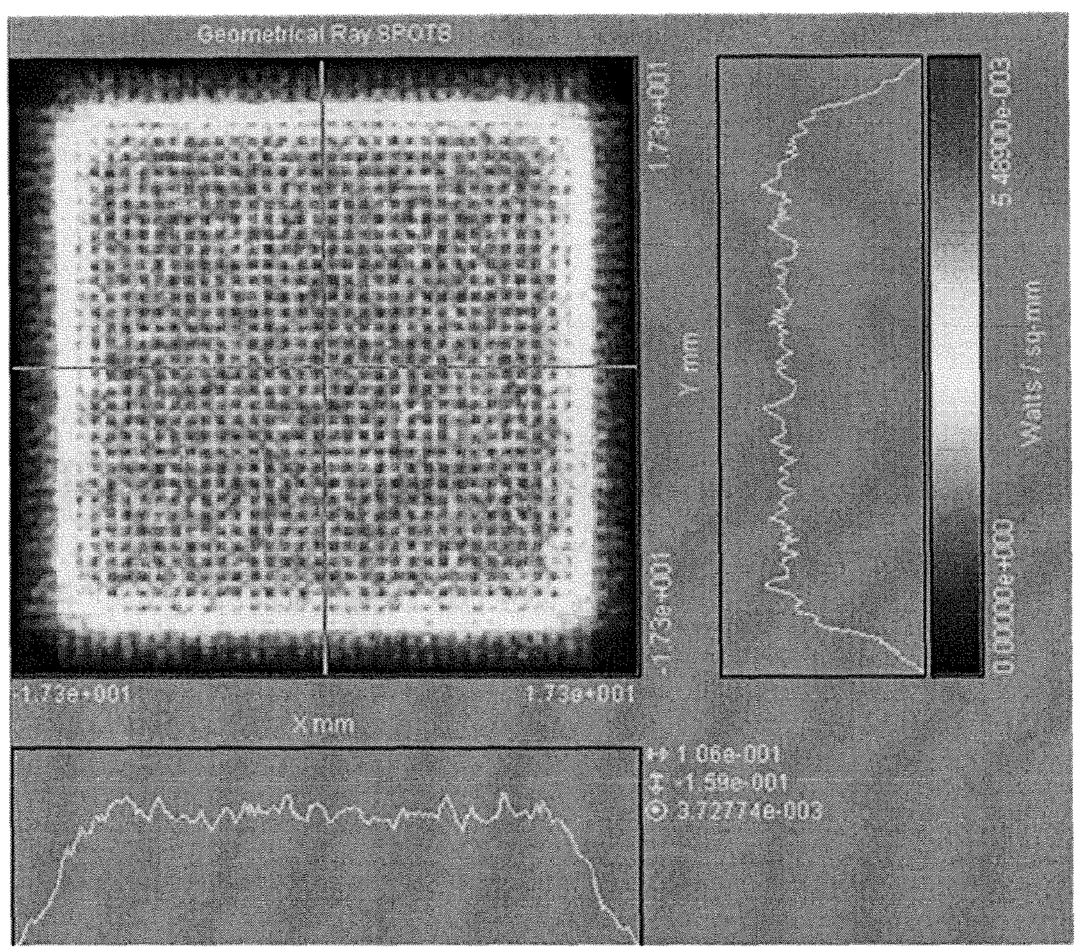
FIG. 5 is an image view showing the intensity of light depending on the distance between an apparatus for measuring the transmittance of a piece of cover glass for a photovoltaic cell according to an embodiment of the invention and the piece of cover glass.

In order to detect this light, the detector 120 is disposed at the rear of the cover glass 10. The detector 120 can detect the light by point detection or scan detection. Here, the detector 120 is disposed in the range where the intensity of the light that has been introduced for accurate transmittance measurement is uniform. In greater detail, as shown in FIG. 4 and FIG. 5, collimated light that has uniform intensity is used for measurement of the transmittance of the cover glass 10. That is, the light that has been emitted from the light source part 110 and been incident into the cover glass 10 is scattered and diverges while passing through the cover glass 10 having the pattern 10*a*. Here, since the size of the detector 120 is smaller than the size of the light that is directed into the front surface of the cover glass, rays of the light that have not arrived at the detector 120 are replaced by rays of the light that have been scattered at the other positions and enter the detector. (Here, the size refers to the area that is irradiated with light or occupied by the detector when viewed from the front.) Therefore, when the uniform collimated light is scattered by the cover glass 10, the intensity of the light that passed through the cover glass 10 is uniformed within a predetermined range. As the distance from the cover glass 10 increases, the range where the intensity of the light is uniform decreases. Thus, when the detector 120 is disposed within the range where the intensity of the light that has passed through the cover glass 10 is uniform, it is possible to measure the transmittance of the light without a loss in the light. Here, the range where the uniformity of light is uniform may be a range where the distance between the cover glass 10 and the detector 120 is 15 mm or less. When the distance between the cover glass 10 and the detector 120 is greater than 15 mm, part of the scattered light is lost on the way to the detector 120 from the cover glass 10, thereby making it impossible to obtain an accurate transmittance measurement. The detector 120 can consist of a photodiode, i.e. a light detection sensor, and a digital multimeter (DMM) connected to the photodiode.

TABLE 1

| | Comparative Examples (%) | Examples (%) |
|---|---|---|
| Sample 1 | 97.966 | 98.672 |
| Sample 2 | 97.521 | 98.407 |
| Sample 3 | 96.369 | 97.084 |
| Sample 4 | 91.010 | 93.524 |

Figure 6:
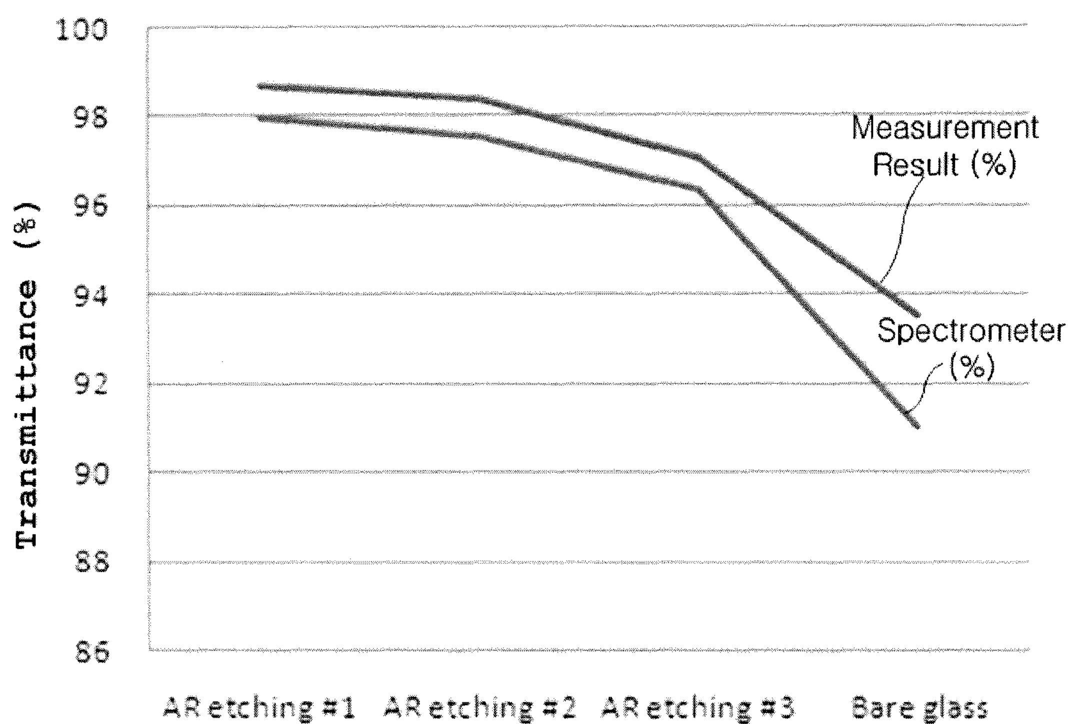
FIG. 6 is a graph showing the results obtained by measuring the transmittance of various types of cover glass using an apparatus for measuring the transmittance of a piece of cover glass for a photovoltaic cell according to an embodiment of the invention and a spectrometer of the related art.

FIG. 6 is a graph showing the results of Table 1, i.e., the results obtained by measuring the transmittance of various types of cover glass using an apparatus for measuring the transmittance of a piece of cover glass for a photovoltaic cell according to an embodiment of the invention and a spectrometer of the related art. Here, Sample 1 to Sample 3 are pieces of cover glass the surface of which is etched in order to prevent reflection, and Sample 4 is a piece of glass which is not etched.

Comparing the results, in all samples, i.e. Sample 1 to Sample 4, the transmittance measurements in Examples that were obtained using the apparatus for measuring the transmittance of a piece of cover glass for a photovoltaic cell according to an embodiment of the invention are higher than the transmittance measurements in Comparative Examples that were obtained using the spectrometer of the related art. This can be analogized as a result that was obtained by measuring the transmittance by minimizing a loss in the light by disposing the detector 120 at the rear of the cover glass 10, specifically, in the range where the intensity of light is uniform. It can also be appreciated that the respective transmittances of the pieces of cover glass the surfaces of which are etched (Sample 1 to Sample 3) are much more improved than the transmittance of the piece of cover glass which is not etched (Sample 4).

The foregoing descriptions of specific exemplary embodiments of the present invention have been presented with respect to the certain embodiments and drawings. They are not intended to be exhaustive or to limit the invention to the precise forms disclosed, and obviously many modifications and variations are possible for a person having ordinary skill in the art in light of the above teachings.

It is intended therefore that the scope of the invention not be limited to the foregoing embodiments, but be defined by the Claims appended hereto and their equivalents.

What is claimed is:

1. An apparatus for measuring the transmittance of a piece of cover glass for a photovoltaic cell, comprising:

a light source part disposed in front of the piece of cover glass, the light source part directing light into the piece of cover glass; and a detector disposed in the rear of the piece of cover glass, the detector detecting light that has been directed into the piece of cover glass and then has passed through the piece of cover glass, wherein:

the detector is disposed within a range where the intensity of the light that has passed through the piece of cover glass is uniform, and the range where the intensity of the light is uniform is such that the detector is distant from the piece of cover glass by 15 mm or less.

2. The apparatus of claim 1, wherein the light source part directs collimated light into the piece of cover glass.

3. The apparatus of claim 2, wherein the light source part comprises:

a light source; and a lens which collimates light that has been emitted from the light source.

4. The apparatus of claim 3, wherein a pin-hole is disposed between the light source and the lens.

5. The apparatus of claim 3, wherein the light source comprises a halogen lamp.

6. The apparatus of claim 1, wherein the size of the detector is smaller than the size of the light that is directed into the piece of cover glass.

7. The apparatus of claim 1, wherein the detector comprises:

a photodiode; and a digital multimeter connected to the photodiode.

8. The apparatus of claims 1, 2, 3, 4, 5, 6 or 7, wherein the piece of cover glass has a pattern formed on a front surface thereof.

* * * * *